United States Patent [19]

Sinaiko

[11] Patent Number: 5,316,015
[45] Date of Patent: May 31, 1994

[54] EXTERNALLY CONTROLLED INTESTINAL CONTENT SAMPLER

[76] Inventor: Robert J. Sinaiko, 450 Sutter St., San Francisco, Calif. 94108

[21] Appl. No.: 922,148

[22] Filed: Jul. 30, 1992

[51] Int. Cl.⁵ .............................................. A61B 5/00
[52] U.S. Cl. ..................................... 128/769; 128/780
[58] Field of Search ............... 128/769, 768, 780, 760; 604/890.1, 891.1, 54, 68, 93, 131, 134, 135, 263, 285, 288, 327, 335; 600/12, 10, 9

[56] References Cited

U.S. PATENT DOCUMENTS

| | | | |
|---|---|---|---|
| 3,057,344 | 10/1962 | Abella et al. | 128/769 |
| 3,118,439 | 1/1964 | Perrenoud | 128/769 |
| 3,315,660 | 4/1967 | Abella | 128/769 |
| 3,319,622 | 5/1967 | Shiner | 128/768 |
| 3,485,235 | 12/1969 | Felson | 128/769 |
| 3,528,429 | 9/1970 | Beal et al. | 604/54 |
| 4,036,214 | 7/1977 | Bucalo | 128/769 |
| 4,154,226 | 5/1979 | Hennig et al. | 600/30 |
| 4,239,040 | 12/1980 | Hosoya et al. | 604/135 |
| 4,257,427 | 3/1981 | Bucalo | 128/769 |
| 4,340,615 | 7/1982 | Goodwin et al. | 427/2 |
| 4,417,360 | 11/1983 | Moasser | 623/2 |
| 4,439,197 | 3/1984 | Honda et al. | 604/891.1 |
| 4,481,952 | 11/1984 | Pawelec | 128/769 |
| 4,507,115 | 3/1985 | Kambara et al. | 604/135 |

FOREIGN PATENT DOCUMENTS

| | | | |
|---|---|---|---|
| 460327 | 12/1991 | European Pat. Off. | 128/769 |
| 9205822 | 4/1992 | PCT Int'l Appl. | 128/769 |
| 665897 | 6/1979 | U.S.S.R. | 128/769 |

*Primary Examiner*—Stephen C. Pellegrino
*Assistant Examiner*—Guy V. Tucker
*Attorney, Agent, or Firm*—Flehr, Hohbach, Test, Albritton & Herbery

[57] ABSTRACT

Intestinal content sampling device having a capsule which is adapted to be swallowed and to pass through the intestinal tract. The capsule has an opening through which a sample can pass and a closure member for closing off the opening once a sample has been obtained. The closure member is held in an open position against a closing force by a magnetically actuated latch which, in the disclosed embodiments, comprises a pendulum which is set into vibration by an externally applied magnetic field to release the latch.

5 Claims, 2 Drawing Sheets

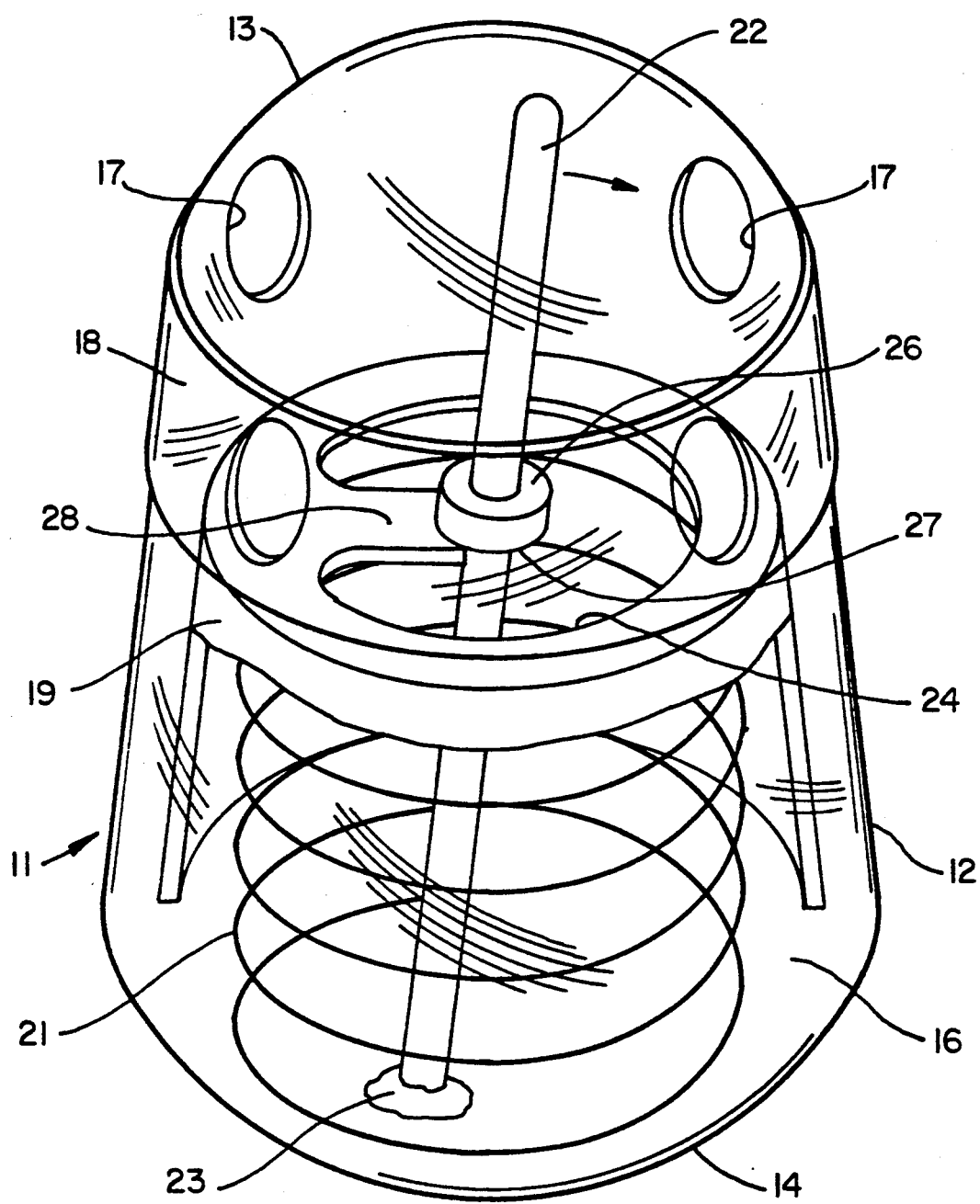
FIG_1

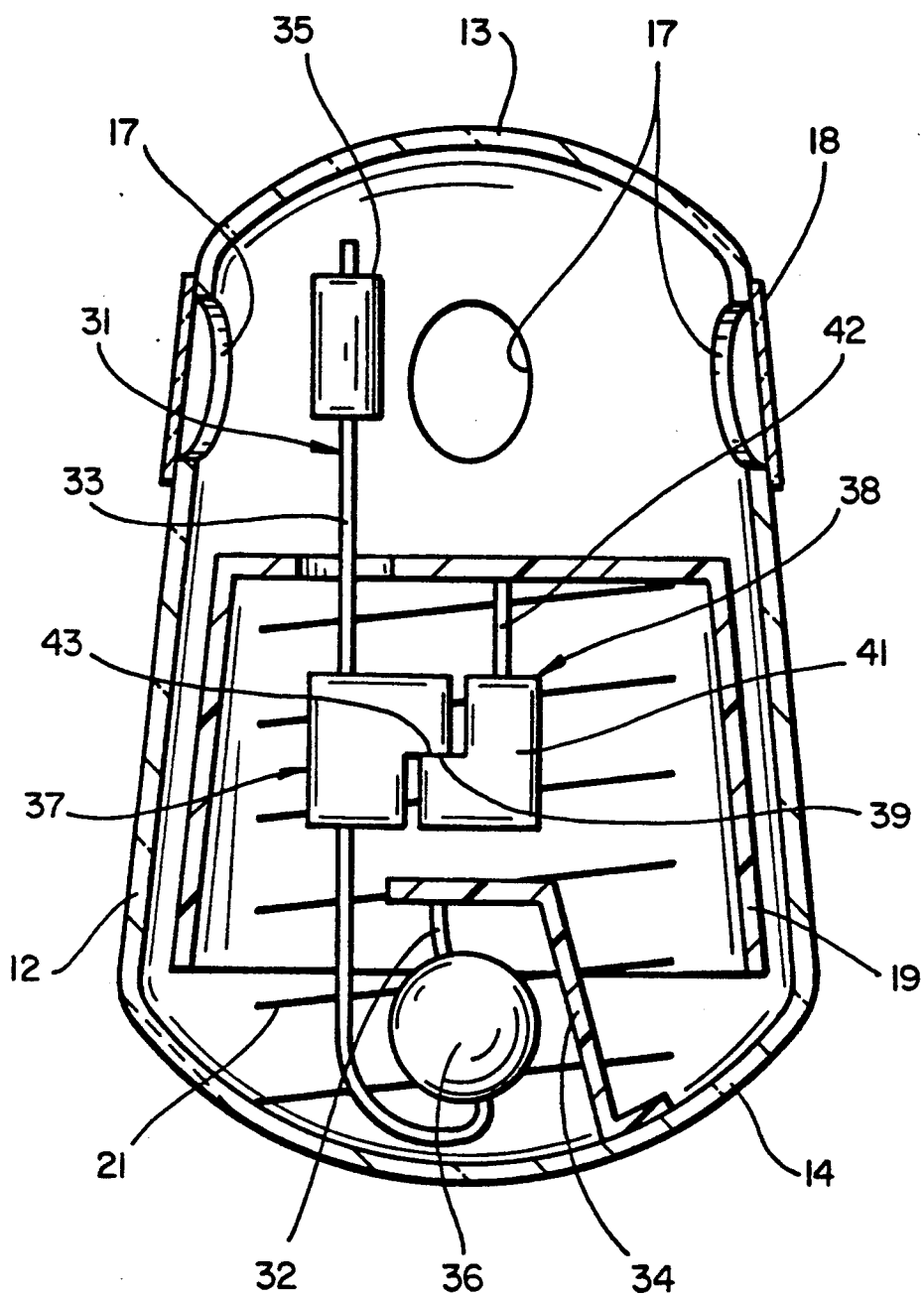
FIG_2

EXTERNALLY CONTROLLED INTESTINAL CONTENT SAMPLER

BACKGROUND OF THE INVENTION

1. Field of the Invention

This invention pertains generally to medical devices and, more particularly, to a device for obtaining a sample from the intestinal tract of a person.

2. Description of Related Art

Heretofore, there have been some attempts to obtain samples from the intestinal tracts of human beings by means of relatively small capsules which are swallowed, then opened to collect a sample as they pass through the intestinal tract. Such devices are particularly useful in the small intestine where it is otherwise difficult to obtain samples for chemical and microbiological analysis.

One example of a swallowable capsule for obtaining samples of gastric and/or intestinal fluids is found in U.S. Pat. No. 4,481,952. That capsule has an inner chamber with an inlet port which is normally sealed off by a film or coating which is dissolved by the fluids in the portion of the body from which the sample is to be obtained. The capsule also has a spring-actuated closure which is held in an open position relative to the port by a restraint fabricated of a material which is dissolved by the sampled fluid. Thus, the capsule is intended to open when it reaches the area in which the sample is to be taken, then close after the sample is obtained to contain the sample and protect it from contamination as capsule continues its passage through other parts of the body. One problem with this type of device is that it does not provide very precise control over the closing of the capsule, with the result that the sample may be lost or become contaminated before the closing occurs.

U.S. Pat. No. 4,239,040 discloses a capsule for discharging drugs into or collecting samples from the body, which utilizes a meltable thread to hold a piston-like element against the force of a spring. Movement of the piston-like element serves to push drugs out of or draw a sample into the capsule, and the thread is melted by a heater which is energized by an electric circuit including a tunable receiver which responds to an externally transmitted electric signal.

U.S. Pat. Nos. 4,439,197 and 4,507,115 shows capsules for discharging medicine or obtaining samples, utilizing shape memory elements to move piston-like elements in response to temperature changes. In the '197 patent, the capsule contains a power source, a switching circuit, and a radio receiver which respond to radio frequency signals to control the temperature of the shape memory element, and in the '115 patent, the shape memory element is heated ultrasonically.

OBJECTS AND SUMMARY OF THE INVENTION

It is in general an object of the invention to provide a new and improved device for obtaining a sample from the intestinal tract of a person.

Another object of the invention is to provide a sampling device of the above character which overcomes the limitations and disadvantages of sampling devices heretofore provided.

These and other objects are achieved in accordance with the invention by providing a sampling device having a capsule with an internal chamber and an opening through which a sample can pass to the chamber, a closure member movable between open and closed positions relative to the opening, means urging the closure member toward the closed position, and magnetically actuated latch means for holding the closure member in the open position and releasing the closure member for movement toward the closed position in response to an externally applied magnetic stimulation.

BRIEF DESCRIPTION OF THE DRAWINGS

FIG. 1 is an isometric view, partly broken away, of one embodiment of an intestinal content sampler according to the invention.

FIG. 2 is a cross-sectional view of another embodiment of an intestinal content sampler according to the invention.

DETAILED DESCRIPTION

As illustrated in FIG. 1, the intestinal content sampler comprises a capsule 11 having a conically tapered side wall 12 and rounded end walls 13, 14. The capsule is fabricated of a material such as plastic and adapted to be swallowed by the patient.

The capsule has an internal chamber 16 and a plurality of openings 17 spaced peripherally about the side wall toward the narrow end of the capsule. The openings provide communication between the chamber and the exterior of the capsule, and are initially closed by a seal 18 fabricated of a material which is dissolved by fluids in the intestinal tract.

A closure member in the form of a piston or plug 19 is mounted within the capsule for movement between advanced and retracted positions relative to openings 17. The piston has a conically tapered side wall or skirt and is adapted to engage the side wall of the capsule to seal the openings when moved toward the narrow end of the capsule. The piston is urged toward the advanced position by a coil spring 21.

Magnetically actuated latch means is provided for holding the piston in the retracted position until a sample has been obtained from the intestinal tract. This means comprises a pendulum having a shaft 22 of ferrous material. One end of the pendulum shaft is attached to the large end of the capsule by a flexible bonding material 23, and the other end of the shaft is free to vibrate in response to magnetic stimulation. The pendulum shaft passes through an opening 24 in the upper wall of the piston, and a collar 26 having an axially facing bearing surface 27 on the lower side thereof is affixed to the shaft. The piston has a radially extending tab 28 which engages the bearing surface when the piston is in the retracted position and is dislodged therefrom by vibration of the shaft.

Operation and use of the embodiment of FIG. 1 is as follows. The capsule is swallowed by the patient with openings 17 sealed by the dissolvable material and piston 19 held in its retracted position by the latch mechanism. When the capsule reaches the intestinal tract, the seal dissolves, allowing a sample to pass to chamber 16 through openings 17. Once the sample has been obtained, the openings are closed to prevent contamination of the sample by fluids from other parts of the body by applying a pulsating magnetic stimulation externally of the patient's body. This causes the pendulum shaft to vibrate, disengaging the latch members, i.e. collar 26 and tab 28, allowing spring 21 to move the piston to the advanced position to close the openings and seal the chamber.

The position of the capsule within the patient can be monitored by suitable means such as ultrasonography or ultrasonic imaging, and the openings can be closed at the precise moment the capsule reaches the desired position. Closure is effected by turning on an electromagnet, such as the magnet in a magnetic resonance imaging machine, to vibrate the pendulum and disengage the latch members.

After the capsule has passed through the patient's body, it is recovered from the stool, washed, and opened to recover the sample.

The embodiment of FIG. 2 is generally similar to that of FIG. 1, and like reference numerals designate corresponding elements in the two embodiments. In the embodiment of FIG. 2, however, the latch mechanism which retains the piston in the retracted position comprises a pendulum having a generally J-shaped shaft 31 with a short leg 32 and a long leg 33. The upper end of the short leg is pivotally mounted to a bracket 34 affixed to the large end of the capsule, with the long leg extending in an upward direction through an opening in the top wall of the piston for vibration in response to a magnetic stimulation. The shaft itself is fabricated of a non-ferrous material, and a mass 35 of magnetically responsive material is mounted on the upper portion of the long leg. A counterweight 36 of magnetically non-responsive material is mounted on the short leg, and the pivot point at the upper end of the short leg is located at the center of gravity of the pendulum assembly. This arrangement serves to prevent inadvertent triggering of the device due to vibration or "jiggling".

A first latch member 37 is affixed to the long leg of the shaft, and a second latch member 38 is pivotally connected to the piston. The first latch member has a bearing surface 39, and the second latch member comprises a block 41 which is suspended from the piston by connectors 42, with a bearing surface 43 which engages surface 39 when the latch members are engaged.

Operation and use of the embodiment of FIG. 2 is similar to that of FIG. 1, with latch members 37, 38 being engaged to hold the piston in the retracted position against the urging of spring 21 until the sample has been obtained. Thereafter, a magnetic stimulation is applied externally of the patient's body to cause the pendulum to vibrate and disengage the latch members. The piston then moves to the advanced position to close the openings and seal the chamber as in the embodiment of FIG. 1.

It is apparent from the foregoing that a new and improved intestinal content sampler has been provided. While only certain presently preferred embodiments have been described in detail, as will be apparent to those familiar with the art, certain changes and modifications can be made without departing from the scope of the invention as defined by the following claims.

I claim:

1. A sampling device for obtaining a sample from the intestinal tract of a person, comprising: a capsule having an internal chamber and an opening through which a sample can pass to the chamber, means for closing the opening prior to obtaining a sample, a closure member movable between open and closed positions relative to the opening, means urging the closure member toward the closed position, a pendulum which vibrates in response to magnetic stimulation, one end of the pendulum being affixed to the capsule, a counterweight attached to the pendulum toward the one end thereof, and latch members attached to the closure member and to the pendulum, said latch members being engageable with each other to hold the closure member in the open position and being disengagable from each other by vibration of the pendulum to release the closure member for movement toward the closed position in response to an externally applied magnetic stimulation.

2. A sampling device for obtaining a sample from the intestinal tract of a person, comprising: a swallowable capsule having rounded ends and a conically tapered side wall disposed about an axis, an opening in the side wall, means for closing the opening to prevent matter from entering the capsule until the capsule reaches the intestinal tract, a closure member movable in an axial direction within the capsule between open and closed positions relative to the opening, means urging the closure member toward the closed position with a resilient force, a pendulum extending axially within the capsule and being adapted to vibrate in response to an externally applied stimulation, and latch members attached to the closure member and to the pendulum for retaining the closure member in the open position when engaged and releasing the closure member for movement toward the closed position when disengaged, said latch members being disengaged by vibration of the pendulum and comprising a generally J-shaped shaft having a long leg and a short leg, means mounting the shaft to the capsule at an outer end of the short leg with the long leg of the shaft being free to vibrate, a counterweight of magnetically non-responsive material mounted on the short leg of the shaft, and a mass of magnetically responsive material mounted on the long leg toward an outer end thereof.

3. The sampling device of claim 2 wherein the latch members comprise an axially facing bearing surface on the pendulum, and a block pivotally connected to the closure member for engagement with and disengagement from the bearing surface.

4. A sampling device for obtaining a sample from the intestinal tract of a person, comprising: a capsule having an internal chamber and an opening through which a sample can pass to the chamber, means for closing the opening prior to obtaining a sample, a closure member movable in an axial direction between open and closed positions relative to the opening, means urging the closure member toward the closed position, a pendulum adapted for vibration in response to an externally applied stimulation having a generally J-shaped shaft with a long leg and a short leg, means mounting the shaft to the capsule at an outer end of the short leg with the long leg of the shaft being free to vibrate, a counterweight mounted on the short leg of the shaft, a mass mounted on the long leg of the shaft toward an outer end thereof, first latch member affixed to the long leg to the shaft, and a second latch member attached to the closure member for engagement with and disengagement from the first latch member, said latch members being disengaged by vibration of the pendulum.

5. The sampling device of claim 4 wherein the first latch member comprises an axially facing bearing surface on the pendulum, and the second latch member comprises a block pivotally connected to the closure member for engagement with and disengagement from the bearing surface.

* * * * *